United States Patent
Chowhan et al.

(10) Patent No.: US 9,446,093 B2
(45) Date of Patent: *Sep. 20, 2016

(54) INJECTABLE AQUEOUS OPHTHALMIC COMPOSITION AND METHOD OF USE THEREFOR

(71) Applicant: Alcon Research Ltd., Forth Worth, TX (US)

(72) Inventors: Masood A. Chowhan, Arlington, TX (US); Thomas C. Hohman, Fort Worth, TX (US); Ernesto J. Castillo, Forth Worth, TX (US); Wesley Wehsin Han, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/057,125

(22) Filed: Oct. 18, 2013

(65) Prior Publication Data

US 2014/0094419 A1 Apr. 3, 2014

Related U.S. Application Data

(63) Continuation of application No. 12/886,988, filed on Sep. 21, 2010, now abandoned.

(60) Provisional application No. 61/244,916, filed on Sep. 23, 2009.

(51) Int. Cl.
| | |
|---|---|
| *A61K 38/16* | (2006.01) |
| *A61K 9/00* | (2006.01) |
| *A61K 47/36* | (2006.01) |
| *A61K 47/42* | (2006.01) |
| *A61K 38/00* | (2006.01) |

(52) U.S. Cl.
CPC ............. *A61K 38/16* (2013.01); *A61K 9/0048* (2013.01); *A61K 9/0051* (2013.01); *A61K 38/00* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 8,313,754 B2 | 11/2012 | Chowhan et al. | |
| 8,846,641 B2 * | 9/2014 | Ketelson et al. | ............... 514/54 |
| 2006/0258698 A1 | 11/2006 | Mudumba et al. | |
| 2007/0203173 A1 | 8/2007 | Mudumba et al. | |
| 2012/0101260 A1 | 4/2012 | Farinas et al. | |

FOREIGN PATENT DOCUMENTS

| | | |
|---|---|---|
| CN | 101027038 A | 8/2007 |
| EP | 0 244 178 * | 11/1987 |
| EP | 0244178 | 11/1987 |
| JP | 2009511496 | 3/2009 |
| WO | WO2006/036510 A1 | 4/2006 |
| WO | 2006086750 A1 | 8/2006 |
| WO | 2007/084765 | 7/2007 |
| WO | WO 2007/084765 * | 7/2007 |
| WO | 2009046198 A2 | 4/2009 |
| WO | 2011/037908 | 3/2011 |

OTHER PUBLICATIONS http://web.archive.org/web/20070613051932/http://www.ems-diasum.com/microscopy/technical/datasheet/19320.aspx , 2 pages, retrieved on Jul. 7, 2015.*
http://web.archive.org/web/20071209031541/http://www.ems-diasum.com/microscopy/products/chemicals/pipes.aspx#19320 , 2 pages, retrieved on Jul. 7, 2015.*
Konish, J. Cosmet., Sci., 49, 335-342.*
PCT International Search Report for corresponding PCT/US2010/049623 with mailing date of Nov. 19, 2010.
PCT International Written Opinion for corresponding PCT/US2010/049623 with mailing date of Nov. 19, 2010.

* cited by examiner

*Primary Examiner* — Satyanarayana R Gudibande
(74) *Attorney, Agent, or Firm* — Jason Derry

(57) ABSTRACT

The present invention is directed to the provision of an ophthalmic composition suitable for intravitreal injection. The composition includes an amount of complexing agent that reacts with one or more endogenous components (e.g., hyaluronic acid) in the eye to form a mass of enhanced viscosity. This mass can aid in creating a desirable release profile of therapeutic agent.

9 Claims, No Drawings

INJECTABLE AQUEOUS OPHTHALMIC COMPOSITION AND METHOD OF USE THEREFOR

CROSS REFERENCE TO RELATED APPLICATION

This application is a continuation of U.S. patent application Ser. No. 12/886,988, filed on Sep. 21, 2010, which claims priority to U.S. Provisional Patent Application Ser. No. 61/244,916, filed Sep. 23, 2009, the entire contents of which are incorporated herein by reference.

TECHNICAL FIELD OF THE INVENTION

The present invention is directed to an injectable aqueous ophthalmic composition. More particularly, the present invention is directed to an injectable aqueous ophthalmic composition that includes a complexing agent (e.g., positively charged polymer or other compound) for enhancing the drug delivery capabilities of the composition when the composition is injected in an eye of human or animal.

BACKGROUND OF THE INVENTION

Intravitreal injections are commonly used to deliver therapeutic agents to the eye, particularly to the vitreous humor of the eye for treatment of ophthalmic maladies such as age related macular degeneration (AMD), diabetic macular edema (DME), inflammation or the like. Intravitreal injections are often particularly desirable since they can provide enhanced bioavailability to a target location (e.g., the retina) of the eye relative to other delivery mechanisms such as topical delivery.

While generally providing a desirable form of drug delivery, intravitreal injections also have drawbacks and can present various different complications. Many therapeutic agents have difficulty penetrating target ocular tissue even after intravitreal injection. In some instances, the penetration difficulty can be caused by poor solubility or hydrophilicity of the therapeutic agent. In other instances, poor permeability due to size, molecular weight or other characteristics of the therapeutic agent can be the cause of poor penetration.

Intravitreal injections can also suffer from other drawbacks. As one example, intravitreal injections having therapeutic agent in the form of particles (e.g., suspended submicron particles or nanoparticles) can obstruct vision if the particles disperse in an undesirable manner. As another example, it can be difficult to consistently provide therapeutic agent close to a target location with an intravitreal injection since varying injection angles and variable eye size can cause significant variability in delivery location. As yet another example, intravitreal injections can result in delivery of undesirably high concentrations of therapeutic agent to a target location or elsewhere particularly when the therapeutic agent is relatively soluble.

In addition to the above, therapeutic agents delivered by intravitreal injections can lack duration of action since the agents can often rapidly disperse within the eye after injection. Such lack of duration is particularly undesirable since it can necessitate greater injection frequency.

In view of the above, it would be particularly desirable to provide an intravitreal injection that overcomes one or any combination of the above discussed drawbacks. As such, the present invention provides an ophthalmic composition, a system and a method that allow for a more desirable intravitreal injection.

SUMMARY OF THE INVENTION

The present invention is directed to an injectable ophthalmic composition. The composition typically includes a therapeutic agent, a complexing agent and water. The complexing agent is typically provided in an amount sufficient to form a mass of enhanced viscosity within a vitreous humor of an eye of a human upon injection of the composition into the eye. The mass of enhanced viscosity will typically release the therapeutic agent by virtue of break down of the mass in the vitreous humor and/or the diffusion of the therapeutic agent out of the mass of enhanced viscosity. Advantageously, this allows release of the therapeutic agent over an extended period of time.

The complexing agent is typically positively charged. Preferred complexing agents may be selected from polyamino acids, galactomannan polymer (e.g., cationic-derivatized galactomannan polymer), a quaternary ammonium compound, a cellulosic polymer or a combination thereof. Such agent will preferably be capable of complexing with endogenous hyaluronic acid, collagen or both in the vitreous to for the mass of enhanced viscosity.

DETAILED DESCRIPTION OF THE INVENTION

The present invention is predicated upon the provision of an ophthalmic composition that is particularly suitable for delivery as an intravitreal injection. The ophthalmic composition typically includes an ophthalmic therapeutic agent, complexing agent and water. Upon injection, the complexing agent complexes (e.g., ionically interacts) with an endogenous component (e.g., hyaluronic acid) of the vitreous to form a mass of enhanced viscosity within the vitreous. Advantageously, the mass can aid in one or more of the following: a) slowing release of the therapeutic agent within the eye; b) inhibiting undesired movement of the therapeutic agent within the eye; c) providing a sustained release vehicle that naturally breaks down in the eye; and/or d) decreasing retinal toxicity of some therapeutic agents by lowering exposure of the retina to high therapeutic concentrations or any combination thereof.

Unless indicated otherwise, all ingredient concentrations are listed as % (w/v).

The therapeutic agent of the ophthalmic composition of the present invention will typically exhibit one or more specific characteristics that would normally be problematic for delivery of that agent as an intravitreal injection. The therapeutic agent may exhibit a relatively low degree of solubility due to hydrophobicity or other property of the agent. Alternatively, the therapeutic may exhibit a relatively high degree of solubility due to hydrophilicity or other property of the agent. Additionally or alternatively, the therapeutic agent may have a relatively high molecular weight, which can affect the ability of the agent to penetrate biological membrane.

The therapeutic agent can be provided in solid, semi-solid or liquid form. It is particularly contemplated that the therapeutic agent may be present in solid state as particles (e.g., submicron or nano-particles) and that the complex (e.g., cationic/anionic polymer complex) for with the complexing agent will entrap the particles and release therapeutic agent by one or more mechanisms, at least some of which are discussed herein. When provided as particles, the average particle size will typically be at least 1 nanometer and more typically at least about 10 nanometers and will typically be less than 10 microns, more typically less than 1 micron and even possibly less than about 500 nanometers.

A therapeutic agent having a relatively low degree of solubility for the present invention means that the therapeutic agent exhibits a solubility in water that is less than 0.01%, more typically less than 0.005%. As used herein, solubility in water is to be determined at 25° C. and atmospheric pressure, unless otherwise specifically stated. These relatively water insoluble therapeutic agents are typically hydrophobic. As such, these agents will typically have a log D that is greater than 0.3, more preferably greater than 0.8, more preferably greater than 1.5 and even possibly greater than 2.7 or even greater than 5.0.

As used herein, log D is the ratio of the sum of the concentrations of all forms of the therapeutic agent (ionized plus un-ionized) in each of two phases, an octanol phase and a water phase. For measurements of distribution coefficient, the pH of the aqueous phase is buffered to 7.4 such that the pH is not significantly perturbed by the introduction of the compound. The logarithm of the ratio of the sum of concentrations of the solute's various forms in one solvent, to the sum of the concentrations of its forms in the other solvent is called Log D:

$$\log D_{oct/wat} = \log([solute]_{octanol}/([solute]_{ionized\ water} + [solute]_{neutral\ water}))$$

Examples of therapeutic agents having a relatively low degree of solubility include, without limitation, the following; steroids (e.g., corticosteroids) such as dexamethasone, prednisolone (e.g., prednisolone acetate), fluoro-steroid (e.g., fluorometholone), triamcinolone acetonide or the like; receptor tyrosine kinase inhibitors (RTKi) with multi-target binding profiles, such as N-[4-(3-amino-1H-indazol-4-yl)phenyl]-N'-(2-fluoro-5-methylphenyl)urea; and/or prostaglandin H synthesis inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, ciprofloxacin, benoxaprofen, nabumetome, etodolac, phenylbutazone, aspirin, oxyphenbutazone.

A therapeutic agent having a relatively high degree of solubility for the present invention means that the therapeutic agent exhibits a solubility in water that is at least 0.3%, more typically at least 1.0%. These relatively water soluble therapeutic agents are typically hydrophilic. As such, these agents will typically have a log D that is less than about 0.1, more typically less than about 0.05 and even possibly less than about 0.01.

Example of therapeutic agents having a relatively high degree of solubility include, without limitation, fluoroquinolones such as moxifloxacin, vancomycin, gatifloxacin or the like as well as proteins and/or peptides such as ranizumab bevacizumab or the like as well as certain anti-viral drugs such as ganciclovir.

A therapeutic agent having a high molecular weight for the present invention means that that the average molecular weight of the agent is at least 1000 daltons, more typically at least 10,000 daltons and even more typically at least 50,000 daltons. The average molecular weight is typically less than 150,000 daltons and possibly less than 80,000 daltons. Examples of therapeutic agents having relatively high molecular weights include, without limitation, ranizumab, bevacizumab, pegaptanib (pegaptanib sodium) or the like.

The term complexing agent, as used herein, is a compound that is capable of complexing with one or more endogenous components of the vitreous for forming a mass of enhanced viscosity. The complexing preferably occurs through ionic interaction (e.g., attraction) between the complexing agent and one or more components of the vitreous although other interaction (e.g., chemical reaction) may alternatively or additionally form the complex. Preferred complexing agent is cationically (i.e., positively) charged such that it can form an ionic complex with endongenous hyaluronic acid, collagen or both in the vitreous to form the mass of enhanced viscosity. It is also preferred that the complexing agent be a positively charged polymer. Still further it is preferred that the complexing agent be biologically compatible. It is also preferred that the complexing agent, the complex formed between the complexing agent and the endogenous vitreous component (e.g., hyaluronic acid) and the mass of enhanced viscosity formed thereby be bioerodible within the vitreous to aid in the gradual breakdown of the mass and/or complex after formation thereof. Formation and breakdown of the mass and/or complex are discussed further below.

There are multiple different compounds that may be employed as a complexing agent. Highly preferred compounds include, without limitation, polyamino acid, galactomannan (e.g., cationic-derivatized), amine compounds, cellulosic compounds (e.g., cationic cellulosic compounds), quaternary ammonium compounds or any combination thereof. Of course, one complexing agent may be classified in more than one of these categories depending upon its chemical characteristics. Each of these complexing agents can be provided in a polymeric and/or positively charged form. The complexing agent will typically be present in the composition of the present invention in an amount that is at least 0.01 w/v %, more typically at least 0.1 w/v % and even more typically at least 0.5 w/v %. The concentration of complexing agent will also typically be no greater than about 10 w/v %, more typically no greater than about 3 w/v % and even possibly no greater than 1.0 w/v %.

Poly-amino acids can include any polymer formed of multiple repeat units of amino acid. Examples include, without limitation, polylysine, polyarginine, polyhistidine or the like. When used, polyamino acid is typically present in the composition at a concentration of at least 0.05 w/v %, more typically at least 0.2 w/v % and even more typically at least 0.7 w/v % and a concentration that is typically less than 10.0 w/v %, more typically less than 5.0 w/v % and even more typically less than 1.4 w/v %.

Polylysine is a preferred polyamino acid. Polylysine is typically of the following chemical formula II:

$$(C_6H_{12}N_2O)_n \quad \text{(I)}$$

wherein n=2 to 10,000.

Exemplary polylysines include poly-L-lysine, poly-D-lysine, racemic Poly-DL-lysine, derivatives thereof and combinations thereof. It is contemplated that any of alpha polylysines, epsilon polylysines, poly-L-lysines, poly-D-lysines, any derivatives thereof, any combinations thereof or the like may be used for the present invention unless otherwise specifically stated. However, poly-ϵ-L-lysine is preferred and, as such, the lysine of the composition may be entirely or substantially entirely poly-ϵ-L-lysine. The term substantially entirely, as it refers to poly-ϵ-L-lysine means at least 70% by weight and more preferably at least 90% by weight of the lysine of the composition is poly-ϵ-L-lysine. Poly-ϵ-L-lysine can be formed in accordance with the following scheme:

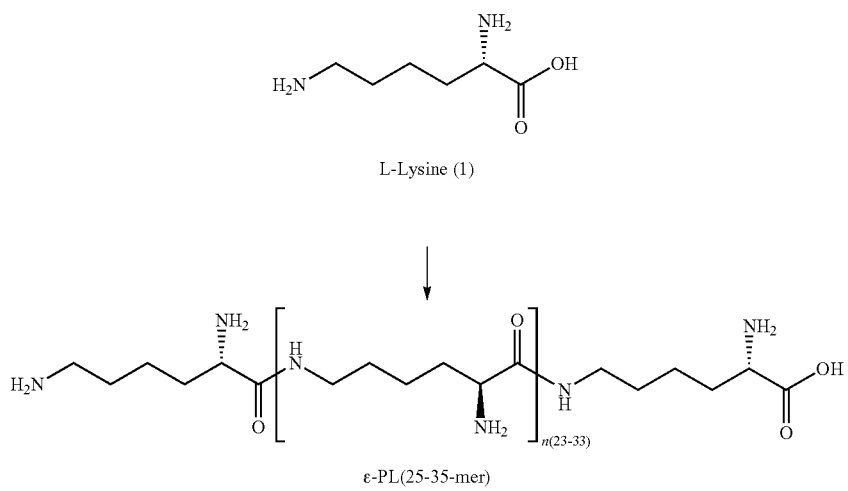

L-Lysine (1)

ε-PL(25-35-mer)

Preferably, any polylysine included in the composition will have a relatively high number average molecular weight. The number average molecular weight of the polylysine is typically at least 50,000, more typically at least 150,000 and even possibly at least 300,000.

Another preferred class of complexing agent is positively charged amine compounds, particularly positively charged amine polymers. Such amine polymers can be primary, secondary, tertiary amines or a combination thereof. Such amine compounds or amine polymers can include or be derived from aromatic or heterocyclic base groups such as aniline, pyridine or others. Nucleosides and polymers derived therefrom are one particularly preferred class of amine compounds suitable as complexing agents for the composition of the present invention. Polysaccharides containing amine groups are also preferred for the composition of the present invention. Examples of preferred amine containing polysaccharides include chitosan and water soluble derivatives of chitosan.

Another preferred class of complexing agent is derivatives of natural polymers, which have been modified to be positively charged and/or soluble in water. Cellulosic polymers are particularly preferred within this class. One particularly preferred positively charged cellulosic polymer is a copolymer of polyethoxylated cellulose and dimethyldiallyl ammonium chloride and has the Cosmetic, Toiletry and Fragrance Association (CTFA) designation of Polyquaternium-4. Suitable such polymers are sold under the tradename CELQUAT SC-230M and CELQUAT SC-240C and are commercially available from Akzo-Nobel. Advantageously, these polymers can be modified to include varying amounts of nitrogen (i.e., nitrogen substitutions) and, through the use of greater or lesser substitutions, the degree of complexing can respectively be raised or lowered. When included, the positively charged natural (e.g., cellulosic) polymers are typically present in the composition at a concentration that is at least at least 0.01 w/v %, more typically at least 0.05 w/v % and even more typically at least 0.2 w/v % and a concentration that is typically less than 4.0 w/v %, more typically less than 1.0 w/v % and even more typically less than 0.4 w/v %.

Quaternary ammonium compounds may also be used as complexing agents for the present invention. A variety of quaternary copolymers of varying quaternization can be synthesized based on homo or copolymers of amino acrylates with methyl, ethyl or propyl side chains. These monomers could also be copolymerized with other nonionic monomers including quaternary acrylic homopolymers such as homopolymers of 2-methacryloxyethyl trimethylammonium chloride and 2-methacryloxyethyl methyl diethyl ammonium bromide and copolymers of quaternary acrylate monomers with water soluble monomers. When included, the quaternary ammonium compounds are typically present in the composition at a concentration that is at least at least 0.01 w/v %, more typically at least 0.05 w/v % and even more typically at least 0.2 w/v % and a concentration that is typically less than 4.0 w/v %, more typically less than 1.0 w/v % and even more typically less than 0.4 w/v %.

One particularly preferred polymer complexing agent is a polymeric quaternary ammonium salt of hydroxyethylcellulose and a trimethyl ammonium chloride substituted epoxide. This complexing agent is both a quaternary ammonium compound and a cellulosic polymer and has the CTFA designation polyquaternium-10. Suitable such polymer is sold under the tradename UCARE JR-30M, which is commercially available from Rhodia or CELQUAT L-200 and H-100, which are commercially available from Akzo Nobel. Another suitable quaternary ammonium/cellulosic compound is an alkyl modified quaternary ammonium salt of hydroxyethyl cellulose and a trimethyl ammonium chloride substituted epoxide having the CTFA designation polyquaternium-24. An example of such polymer is sold under the tradename QUATRISOFT LM-200 and is commercially available from Amerchol Corp., Edison, N.J. Other particularly preferred polymer complexing agents, which are both quaternary ammonium compounds and cellulosic polymers, include various quaternary ammonium salts of hydroxyethyl cellulose sold under the tradename SOFTCAT and commercially available from The Dow Chemical Company, Midland, Mich.

Another preferred polymer complexing agent is galactomannan polymer, particularly cationic-derivatized galactomannan polymer. Particularly preferred is positively charged guar. Guar (e.g., guar gum) or other galactomannan polymer substituted with positively charged chemical moieties are particularly desirable. Such galactomannan polymer will typically have a cationic degree of substitution (DS) with a lower limit of 0.01 and an upper limit of 3.0%, more preferably a lower limit of 0.1 or 0.3% and an upper limit of 2.5%. The galactomannan, particularly in the case of guar gum, typically has a number weight average molecular weight (MW) with a lower limit of 50,000 and an upper limit of about 1,000,000, more preferably a lower limit of 100,000 or 300,000 and an upper limit of about 700,000. One particularly preferred galactomannan is a positively charged guar gum such as O-[2-hydroxy-3-(trimethylamonium)propyl]chloride guar, which is commercially available under the tradename C261N from Cosmedia. Advantageously, such galactomannan polymer (e.g., guar gum) compounds will typically exhibit low toxicity. When included, the galactomannan polymer is typically present in the composition at a concentration that is at least at least 0.04 w/v %, more typically at least 0.20 w/v % and even more typically at least 0.5 w/v % and a concentration that is typically less than 7.0 w/v %, more typically less than 3.0 w/v % and even more typically less than 1.2 w/v %.

The composition of the present invention may be formulated as a solution, a suspension or otherwise. Typically the composition is aqueous and comprises at least 50% and more typically at least 95% water.

Since the composition of the present invention is typically formulated to be suitable for intravitreal injection, the composition will typically be composed of only or substantially only complexing agent, therapeutic agent and water. As used herein, substantially only complexing agent, therapeutic agent and water means that the composition includes less than 5.0 w/v %, more typically less than 4.0 w/v % and even more preferably less than 2.0 w/v % of any ingredients other that complexing agent, therapeutic agent and water.

If other excipients are included, they are typically included in low concentrations. Other suitable excipients can include, without limitation, buffers, salts, surface active agents (e.g., surfactants), polymers, tonicity agents, combinations thereof or the like. For suspensions, a suspending agent may be employed. Particularly preferred suspending agents include, without limitation, polymers such as polysaccharides (e.g., xanthan gum, carboxymethylcellulose, chondroitin sulfate) and carboxyvinyl polymer.

Since the composition of the present invention will typically be administered as an intravitreal injection, the invention also includes a method of delivery. In the method, the composition is typically located within a syringe, the needle of the syringe is then inserted into an eye (e.g., an eye of a human) and the composition is then expelled into the eye. Prior to injection, the composition can be located within the syringe using the syringe to draw the composition from a unit dose container. Alternatively, a pre-filled syringe can contain the composition. An individual (e.g., a doctor) typically inserts the needle into the eye and then uses a plunger of the syringe to expel the composition from inside the syringe into the vitreous (i.e., vitreous fluid) of the eye. Typically the volume of the injection will be at least 1 μL, more typically at least 10 μL and even possibly at least 100 μL and will typically be less than 1000 μL.

Upon delivery, the composition, and particularly the complexing agent, interacts with components of the vitreous to form a mass of enhanced viscosity. As used herein, the term enhanced viscosity suggests a viscosity that is greater than the viscosity of the vitreous fluid at body temperature (i.e., 37 degrees Celcius). The term also suggests that the viscosity of the mass is greater than the viscosity of the composition prior to injection. Preferably, the enhanced viscosity is at least 105%, more typically at least 120% and even more typically at least 140% the viscosity of the vitreous fluid and/or the composition. The therapeutic agent, upon formation of the mass, is dispersed through the mass. For forming the mass of enhanced viscosity, the complexing agent may interact with various components known to be naturally within the vitreous, however, it is preferable that the complexing agent at least interact with endogenous hyaluronic acid, collagen or both within the vitreous. In a preferred embodiment, the complexing agent complexes with the endogenous hyaluronic acid to form a gel (e.g., hydrogel) within the vitreous. For forming this complex, it is highly preferred that the complexing agent be positively charged.

After formation, the mass of enhanced viscosity breaks down and/or the therapeutic agent diffuses out of the mass over an extended time period for releasing therapeutic agent. For relatively soluble and insoluble therapeutic agents, which may be of various different particles sizes, the extended time period is typically at least two hours, more typically at least 8 hours and even possibly at least 24 or 48 hours. The extended time period will often be less than 120 or 60 days. Over this time period, the complexing agent and/or the mass of enhanced viscosity breaks down through biodegradation and potentially other mechanisms as well. Preferably, the lysine, particularly polylysine, breaks down into its amino acid lysine form such that it can be eliminated from the vitreous through natural pathways.

The mass may be formed in any location within the vitreous. However, for many diseases of the retina, it is desirable that the mass be formed close to the fovea. As such, it is contemplated that the entire mass be formed within 10 millimeters, more typically within 5 millimeters and even possibly within 3 millimeters of the fovea.

The present invention can provide a variety of advantages depending upon the embodiment of the invention. For suspensions, which are typically used for the relatively hydrophobic/insoluble therapeutic agents, the enhanced viscosity mass can inhibit the therapeutic agent particles from settling to the bottom of the eye. For relatively hydrophilic/soluble therapeutic agents, the enhanced viscosity mass can inhibit dispersion of the therapeutic agent such that larger amounts of therapeutic agents can be injected at one time without undesirably high amounts of the agent being quickly dispersed within the eye and/or without requiring a relatively high frequency of administration of composition containing therapeutic agent. It is contemplated that the composition of the present invention may be administered less frequently than once every 48 hours, more preferably less than once every 5 days, even more preferably less than once every 10 days, still more preferably less than once every 20 days and even possibly less than once every 30 days. The composition will typically be administered at least once every 60 days. Additionally, the complexing agent may have an additional ability to inhibit dispersion of charged therapeutic agents through charge interaction.

It has also been found that, depending upon the type of complexing agent in the composition, the amount of complexing agent in the composition can be tailored to result in a mass of enhanced viscosity that has a density substantially similar to the density of the vitreous fluid. When such densities are so matched, the mass of enhanced viscosity will remain substantially stationary relative to the eye for a substantial portion of the extended time period of therapeutic agent release. In such an embodiment, the density of the mass upon formation is less than 15% and more preferably less than 5% higher or lower than the density of the vitreous fluid.

As yet another advantage, the compositions of the present invention can be more easily injected into the eye relative to other injections. Since the mass of enhanced viscosity is formed upon injection rather that prior to injection, the composition can be more easily injected, particularly through a fine gauge needle, relative to a composition that is already of enhanced viscosity prior to injection. As still another advantage, the ability of the mass of enhanced viscosity to inhibit rapid dispersion of small particles of therapeutic agent can help the composition, particularly when formulated as a suspension, avoid obstruction of vision.

The composition, particularly intravitreal injections of the composition, can be used to treat a variety of ophthalmic maladies. It is particularly desirable for treating diseases such as age related macular degeneration (AMD), diabetic macular edema (DME), retinal infections, viral infections, inflammation, endophthalmitis or the like.

EXAMPLES

Example 1

Poly-L-lysine aqueous solution (1%) was injected into a matrix material. The amine groups on the poly-lysine had a pKa value of approximately 10.5 and were positively charged and soluble in acidic to neutral solution with a charge density dependent upon pH. The matrix material was formed of vitreous fluid attained from excised pig eyes or rabbit eyes. As such, the matrix material typically included hyaluronic acid and collagen. Upon injection, the poly-L-lysine formed masses of enhanced viscosity with the hyaluronic acid and/or collagen in the form of gel complexes within the matrix material. Thereafter, each of the masses of enhanced viscosity slowly eroded over various extended time periods.

Example 2

Cationic Guar C261N, 1% aqueous solution, was injected into a matrix material. The matrix material was formed of vitreous fluid attained from excised pig eyes or rabbit eyes. As such, the matrix material typically included hyaluronic acid and collagen. Upon injection, the cationic guar formed masses of enhanced viscosity with the hyaluronic acid and/or collagen in the form of gel complexes within the matrix material. Thereafter, each of the masses of enhanced viscosity slowly eroded over various extended time periods.

Example 3

Chitosan and water soluble derivatives of chitosan such as lactate chitosan and carboxy methyl chitosan were injected into a matrix material. The amine groups on the chitosan had a pKa value of approximately 6.5 and were positively charged and soluble in acidic to neutral solution with a charge density dependent upon pH and % degree of acetylation-value. The matrix material was formed of vitreous fluid attained from excised pig eyes. As such, the matrix material typically included hyaluronic acid and collagen. Upon injection, the chitosan and its derivatives each formed masses of enhanced viscosity with the hyaluronic acid and/or collagen in the form of gel complexes within the matrix material. Thereafter, each of the masses of enhanced viscosity slowly eroded over various extended time periods.

Example 4

Various grades of quaternary ammonium salts of hydroxyethylcellulose (SOFTCAT polymers) were injected into the matrix material described in example 1. The polymers each formed masses of enhanced viscosity with the hyaluronic acid and or collagen in the form of gel complexes within the matrix material. Thereafter, each of the masses of enhanced viscosity slowly eroded over various extended time periods.

Example 5

Various grades of CELQUAT polymers were injected into the matrix material described in example 1. The polymers each formed masses of enhanced viscosity with the hyaluronic acid and/or collagen in the form of gel complexes within the matrix material. Thereafter, each of the masses of enhanced viscosity slowly eroded over various extended time periods.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An injectable ophthalmic composition, comprising:
   a therapeutic antibody;
   complexing agent in the composition at a concentration that is at least 0.01 w/v % but no greater than 10 w/v % of the composition wherein, upon injection into a vitreous humor of an eye of a human, the complexing agent forms a complex with endogenous hyaluronic acid, collagen or both to form a mass of enhanced viscosity within the vitreous humor and wherein the complexing agent is a positively charged galactomannan polymer, and
   water;
   wherein the mass of enhanced viscosity breaks down in the vitreous humor to release the antibody and/or the antibody diffuses out of the mass of enhanced viscosity over an extended period of time of at least 8 hours and wherein, upon formation, the mass of enhanced viscosity has a viscosity greater than the viscosity of the injectable composition at the time of injection and wherein the composition is contained within a syringe, the syringe having a needle suitable for intravitreal injection.

2. The composition as in claim 1 wherein the antibody is entrapped as nanoparticles, submicron particles, microparticles or a combination thereof.

3. The composition as in claim 1 wherein the enhanced viscosity of the mass, upon formation, is less than 5% higher or lower than the viscosity of the vitreous fluid.

4. The composition as in claim 3 wherein the mass of enhanced viscosity moves no more than 5 millimeters during at least 50% of the extended period of time.

5. The composition as in claim 1 wherein the extended period of time is at least 20 days.

6. The composition as in claim 1 wherein the composition is free of hyaluronic acid.

7. An injectable ophthalmic composition, comprising:
a therapeutic antibody;
complexing agent in the composition at a concentration that is at least 0.01 w/v % but no greater than 10 w/v % of the composition wherein, upon injection into a vitreous humor of an eye of a human, the complexing agent forms a complex with endogenous hyaluronic acid, collagen or both to form a mass of enhanced viscosity within the vitreous humor and wherein the complexing agent is positively charged galactomannan polymer; and
water;
wherein the composition is contained within a syringe, the syringe having a needle suitable for intravitreal injection and wherein the mass of enhanced viscosity breaks down in the vitreous humor to release the antibody and/or the antibody diffuses out of the mass of enhanced viscosity over an extended period of time and wherein the extended time period is at least 20 days and wherein, upon formation, the mass of enhanced viscosity has a viscosity greater than the viscosity of the injectable composition at the time of injection.

8. The composition as in claim 7 wherein the antibody is entrapped as nanoparticles, submicron particles, microparticles or a combination thereof and wherein the composition is free of hyaluronic acid.

9. The composition as in claim 7 wherein the complexing agent is such that the mass of enhanced viscosity moves no more than 5 millimeters during at least 50% of the extended period of time.

\* \* \* \* \*